United States Patent
Shin et al.

(10) Patent No.: US 10,959,981 B2
(45) Date of Patent: Mar. 30, 2021

(54) COMPOSITION FOR PREVENTING OR TREATING CLIMACTERIC SYMPTOMS COMPRISING SOYBEAN EXTRACT COMPRISING COUMESTROL AS AN ACTIVE INGREDIENT

(71) Applicant: AMOREPACIFIC CORPORATION, Seoul (KR)

(72) Inventors: Hyun Jung Shin, Yongin-si (KR); Hyun Woo Jeong, Yongin-si (KR); Ji Hae Lee, Yongin-si (KR); Dae Jin Min, Yongin-si (KR); Dae Bang Seo, Yongin-si (KR); Sang Jun Lee, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 259 days.

(21) Appl. No.: 15/989,544

(22) Filed: May 25, 2018

(65) Prior Publication Data
US 2018/0271830 A1    Sep. 27, 2018

Related U.S. Application Data

(62) Division of application No. 14/888,623, filed as application No. PCT/KR2014/004012 on May 7, 2014, now Pat. No. 10,111,856.

(30) Foreign Application Priority Data

May 2, 2014 (KR) ........................ 10-2014-0053471

(51) Int. Cl.
*A61K 31/37* (2006.01)
*A61K 36/48* (2006.01)

(52) U.S. Cl.
CPC .............. *A61K 31/37* (2013.01); *A61K 36/48* (2013.01); *A23V 2002/00* (2013.01); *A61K 2236/19* (2013.01)

(58) Field of Classification Search
None
See application file for complete search history.

(56) References Cited

U.S. PATENT DOCUMENTS

| | | | |
|---|---|---|---|
| 7,470,438 B1 * | 12/2008 | Fagot | A61Q 19/08 424/725 |
| 8,829,205 B2 | 9/2014 | Jeon et al. | |
| 2002/0160028 A1 | 10/2002 | Pyo et al. | |
| 2005/0137176 A1 | 6/2005 | Ferraris et al. | |
| 2012/0289714 A1 | 11/2012 | Jeon et al. | |
| 2013/0028921 A1 | 1/2013 | Jeon et al. | |
| 2013/0071342 A1 | 3/2013 | Jeon et al. | |
| 2013/0090377 A1 | 4/2013 | Jeon et al. | |

FOREIGN PATENT DOCUMENTS

| | | |
|---|---|---|
| CN | 1475227 A | 2/2004 |
| JP | 2004-504276 A | 2/2004 |
| JP | 2004-067590 A | 3/2004 |
| JP | 2005-179366 A | 7/2005 |
| JP | 2006-189675 A | 7/2006 |
| KR | 10-2002-0000980 A | 1/2002 |
| KR | 10-2011-0089107 A | 8/2011 |
| KR | 10-2011-0110052 A | 10/2011 |
| KR | 10-2011-0110053 A | 10/2011 |
| WO | 01/97769 A1 | 12/2001 |
| WO | 02/00183 A2 | 1/2002 |
| WO | 2011/093686 A2 | 8/2011 |
| WO | 2012/006750 A1 | 1/2012 |

OTHER PUBLICATIONS

Office Action from corresponding Japanese Application No. 2016-512830, dated Feb. 5, 2019.
Hee Young Jeon, et al., "Effect of Aspergillus oryzae-Challenged Germination on Soybean Isoflavone Content and Antioxidant Activity", J. Agric. Food Chem., 2012, vol. 60, pp. 2807-2814.
Eun Soon Yang, et al., "The Effects of Genistein on the Proliferation and Type I pN Collagen Synthesis in Aged Normal Human Fibroblasts", Kor. J. Microbiol. Biotechnol., 2007, vol. 35, No. 4, pp. 316-324.
Pharma Medica, vol. 22 No. 4 pp. 55-58, 2004.
Fragrance Journal, vol. 28 pp. 129-131, Dec. 2000.
International Search Report for PCT/KR2014/004012, dated Aug. 7, 2014.
Office Action from Japanese Patent Application No. 2016-512830 (dated Mar. 6, 2018).
Office Action from Japanese Patent Application No. 2016-512830 (dated Nov. 28, 2017).
Extended European Search Report and Written Opinion from EP 14794096.9 (dated Dec. 22, 2016).
Tripathi et al., "Soybean—a consummate functional food: A review," Journal of Food Science and Technology, 42(2):111-119 (2005).
Jeon et al., "Effect of Aspergillus oryzae-challenged germination on soybean isoflavone content and antioxidant activity," J. Agric. Food Chem., 60(11): 2807-2814 (2012).
Jeong et al., "Effects of germination and osmopriming treatment on enhancement of isoflavone contents in various soybean cultivars and cheonggukjang (fermented unsalted soybean paste)" J Food Sci, 73(8):H187-94 (2008).

* cited by examiner

*Primary Examiner* — Susan Hoffman
(74) *Attorney, Agent, or Firm* — Merchant & Gould P.C.

(57) ABSTRACT

The present invention relates to a composition for, inter alia, preventing or treating a climacteric disease, or preventing or improving a climacteric skin symptom comprising a soybean extract comprising coumestrol as an active ingredient, and more specifically relates to a composition for, inter alia, preventing or treating a climacteric disease, or preventing or improving a climacteric skin symptom comprising a germinated and fermented soybean extract comprising coumestrol as an active ingredient.

9 Claims, 4 Drawing Sheets

COMPOSITION FOR PREVENTING OR TREATING CLIMACTERIC SYMPTOMS COMPRISING SOYBEAN EXTRACT COMPRISING COUMESTROL AS AN ACTIVE INGREDIENT

This application is a Division of U.S. application Ser. No. 14/888,623 filed 2 Nov. 2015, now U.S. Pat. No. 10,111,856, which is a U.S. National Stage Application under 35 U.S.C. § 371 of International Patent Application No. PCT/KR2014/004012 filed 7 May 2014, which claims the benefit of priority to Korean Patent Application No. 10-2013-0050771 filed 6 May 2013 and to Korean Patent Application No. 10-2014-0053471 filed 2 May 2014, the disclosures of all of which are hereby incorporated by reference in their entireties. The International Application was published in Korean on 13 Nov. 2014 as WO 2014/182044.

TECHNICAL FIELD

The present disclosure relates to a composition for preventing a climacteric disease, which contains a bean extract containing coumestrol as an active ingredient. More particularly, it relates to a composition for preventing a climacteric disease, which contains a germinated and fermented bean extract containing coumestrol as an active ingredient.

BACKGROUND ART

Climacteric symptoms refer to the symptoms caused by the decreased secretion of male or female hormones. For women in particular, climacteric diseases occur for about 2-10 years around menopause due to a decrease in the ovaries' production of estrogen and cause such symptoms as high fever, sweating, insomnia, depression, urinary incontinence, pain, osteoporosis, myocardial infarction, stroke and hypertension.

Osteoporosis, which is the most representative disease among the climacteric symptoms, refers to a symptom where total bone mass decreases due to increased activity of osteoclasts as compared to that of osteoblasts. The onset of osteoporosis leads to decreased width of cortical bone, expansion of the marrow cavity and decrease in bone density, making the bone more porous. The physical strength of bone is decreased with the progress of osteoporosis, resulting in back pain and joint pain and making the bone break easily even by a slight impact.

For prevention and treatment of the climacteric symptoms, hormone replacement therapy, nonsteroidal drugs, pharmacotherapies for treatment of osteoporosis, or the like have been developed. At present, the hormone replacement therapy is used as the most effective method. However, prolonged hormone administration is known to cause side effects such as increased risk of cancer, headache, weight gain, etc. Accordingly, development of a therapeutic agent derived from a naturally occurring substance, which is safer and more effective, is urgently needed.

DISCLOSURE

Technical Problem

The present disclosure is directed to providing a composition containing a natural extract which is effective for climacteric symptoms or diseases.

Technical Solution

In an aspect, the present disclosure provides a pharmaceutical composition for preventing or treating a climacteric disease, which contains a germinated and fermented bean extract containing coumestrol as an active ingredient.

In another aspect, the present disclosure provides a health food composition for preventing or improving a climacteric disease, which contains a germinated and fermented bean extract containing coumestrol as an active ingredient.

In another aspect, the present disclosure provides a cosmetic composition for preventing or improving a climacteric skin symptom, which contains a germinated and fermented bean extract containing coumestrol as an active ingredient.

Advantageous Effects

A composition of the present disclosure, which contains a germinated and fermented bean extract containing coumestrol as an active ingredient, can be usefully used to prevent, treat and improve a climacteric disease or a climacteric symptom. Specifically, the composition of the present disclosure can relieve weight gain during the climacteric period, can recover bone density to a level similar to that before the climacteric period and can relieve decrease in skin thickness and skin elasticity during the climacteric period. In addition, since the composition of the present disclosure can also relieve transepidermal water loss during the climacteric period, can activate estrogen and can decrease the amount of MMP1 which degrades collagen and increase the amount of procollagen at the same time, it can be usefully used for a climacteric disease or a climacteric symptom. Also, the composition of the present disclosure, which contains a natural product as an active ingredient, lacks tolerance even when used for a long time and has few side effects.

BEST MODE

In an aspect, the present disclosure relates to a pharmaceutical composition for preventing or treating a climacteric disease, which contains a germinated and fermented bean extract containing coumestrol as an active ingredient.

In another aspect, the present disclosure relates to a health food composition for preventing or improving a climacteric disease, which contains a germinated and fermented bean extract containing coumestrol as an active ingredient.

In another aspect, the present disclosure relates to a cosmetic composition for preventing or improving a climacteric skin symptom, which contains a germinated and fermented bean extract containing coumestrol as an active ingredient.

In the present disclosure, the "bean" may be any plant in the family Fabaceae that can be germinated and contains coumestrol. Specifically, the bean may be bean for making bean paste or tofu, bean for making bean sprouts, bean for boiling with rice, or green bean. The bean varieties for bean paste or tofu include daepung, hojang, jangwon, daehwang, sodam, songhak, daewon, jinpum, danbaek, duyu, shinpaldal, taegwang, manli, jangsu, muhan, baegun, saeal, hwangkeum, jangyeop, etc. The bean varieties for bean sprout include shinhwa-kong, sowon-kong, anpyeong, seonam, dachae, sorok, soho, somyeong, dawon, pungsan-namul, iksan-namul, sobaek-namul, gwangan, danyeop, eunha, etc. The bean varieties for rice cooking include cheongja, heukcheong, galmi, seonheuk, geomjeong-kong, ilpumgeomjeong-kong, etc. And, the bean varieties for green bean include daol, shinrok, saeul, geomjeongeul, seokryang-putkong, hwaeom-putkong, etc.

More specifically, in the present disclosure, the "bean" may be one or more selected from a group consisting of seoritae (*Glycine max* Merr.), seomoktae (*Rhynchosia nolubilis*), black soybean (*Glycine max* (L.) Merr.), blue bean (*Glycine max* Merr.), yellow bean (*Glycine max* Merr.), field bean (*Vicia faba*), kidney bean (*Phaseolus vulgaris*), pinto bean (*Phaseolus vulgaris* L.), small red bean (*Vigna angularis*), small black bean (*Phaseolus angularis* F. Wight), sprouting bean (*Glycine max* (L.) Merr.) and soybean (*Glycine max*).

In the present disclosure, the "germinated and fermented bean" refers to a bean which has been germinated and fermented simultaneously or sequentially.

In an aspect of the present disclosure, the condition of one or more of the germination and fermentation is not particularly limited as long as the germination and fermentation can occur continuously. For example, the condition of the germination or fermentation may be as follows.

For example, the germination may be performed by contacting at least part of the bean with oxygen or air.

The germination may be performed in a reactor which contains 20-80 vol %, specifically 40-60 vol %, more specifically 45-55 vol %, of a medium based on the volume of the reactor.

The medium used in the germination is not particularly limited as long as the germination and/or fermentation can be achieved satisfactorily. Specifically, a liquid nutrient medium, more specifically a potato dextrose broth (PDB), may be used. In another aspect of the present disclosure, the medium may contain 0.001-10 wt %, specifically 0.1-5 wt %, more specifically 0.5-2 wt %, of a sugar based on the total weight of the medium.

In an aspect of the present disclosure, the germination may be performed by inoculating 1-50 vol %, specifically 5-20 vol %, more specifically 6-12 vol %, of the bean to the reactor based on the volume of the reactor.

In an aspect of the present disclosure, the germination may be performed by supplying oxygen or air at maximum. For example, when the germination is performed in a 5000-mL reactor, oxygen or air may be supplied at a rate of 2,500 vvm/m. And, when the germination is performed in a 3-L reactor, oxygen or air may be supplied at a rate of 15,000 vvm/m. The germination may be achieved satisfactorily by supplying sufficient oxygen or air.

In an aspect of the present disclosure, the germination may be performed at a temperature of 20-35° C., specifically 20-30° C. In another aspect of the present disclosure, the germination may be performed under a shaded condition. In another aspect of the present disclosure, the germination may be performed for 2-10 days. For example, after the germination is performed for 2 days, germination and fermentation may be performed for 6-8 days simultaneously or with a time gap.

The fermentation may be performed by contacting at least part of the bean with a microorganism.

Specifically, the fermentation may be performed by inoculating a microorganism to the bean for 1-10 times, specifically 1-5 times, more specifically 1-3 times. Through this process, the microorganism may come in better contact with the bean. In an aspect of the present disclosure, the microorganism may be any microorganism known in the art that can ferment bean, without limitation. Specifically, it may be a fungus, yeast or a lactic acid bacterium. More specifically, the fungus may be a microorganism in the genus *Aspergillus*, *Penicillium* or *Monascus*, and the microorganism may be one or more selected from a group consisting of *Aspergillus niger*, *Aspergillus sojae*, *Aspergillus oryzae* and *Bifidobacterium infantis*.

The fermentation may be performed by any method without limitation as long as the microorganism can come in contact with the bean. For example, the microorganism may be brought into contact with the bean by applying a suspension solution of spores of the microorganism on the surface of the cotyledon of the bean or by adding a powder of the microorganism to a medium containing the bean.

In the fermentation process, 0.05-2 wt %, specifically 0.75-2 wt %, more specifically 1.0-2.0 wt %, of the microorganism may be brought into contact with the bean based on the weight of the medium.

When preparing the "germinated and fermented bean", the germination and fermentation may be performed simultaneously by contacting the bean with oxygen or air in the state where the bean is in contact with the microorganism. Specifically, the bean may be contact with the oxygen or air in the state where the bean is immersed in a medium containing the microorganism.

When preparing the "germinated and fermented bean", the germination and fermentation may be performed sequentially, for example, by performing germination and then performing fermentation, or by performing fermentation and then performing germination. Specifically, after germination is performed for 2 days, germination and fermentation may be performed for 6-8 days simultaneously or sequentially.

When preparing the germinated and fermented bean, the bean may be sterilized by washing the bean with one or more of sterile water, ethanol and sodium hypochlorite, specifically sterile water.

The bean containing coumestrol which has been obtained through the above-described processes may be extracted with water or ethanol at room temperature or elevated temperature. The resulting extract may be completely concentrated, dispersed again in water and then fractionated with equal amount of one or more solvent selected from hexane, dichloromethane, chloroform, ethyl acetate, butanol, ethanol, methanol and water to obtain a bean extract containing coumestrol. However, the extraction method is not limited thereto and any extraction method may be used to obtain a final extract containing coumestrol.

In the present disclosure, the "coumestrol" may have a structure of Chemical Formula 1.

[Chemical Formula 1]

In the pharmaceutical composition or the health food composition according to an aspect of the present disclosure, the climacteric disease may include a muscle disease, a bone disease, a heart disease, a skin disease or obesity associated with the climacteric period.

The muscle disease may be rheumatoid arthritis or degenerative arthritis associated with the climacteric period; the bone disease may be osteoporosis, back pain, rickets, osteomalacia or Paget's disease of bone associated with the climacteric period; the heart disease may be angina or arteriosclerosis associated with the climacteric period; or the skin disease may be skin redness or skin dryness.

In the cosmetic composition according to an aspect of the present disclosure, the climacteric skin symptom may specifically include skin redness, obesity, change in skin thickness, decreased skin elasticity or skin dryness. But, without being limited thereto, all the change in skin conditions associated with the climacteric period is included.

The pharmaceutical composition according to an exemplary embodiment of the present disclosure may contain a pharmaceutical adjuvant such as an antiseptic, a stabilizer, a hydrating agent, an emulsification accelerator, a salt and/or buffer for osmotic pressure control, etc. and other therapeutically useful substance(s), and may be prepared into various formulations for oral or parenteral administration according to a commonly employed method.

Formulations for oral administration include, for example, a tablet, a pill, a hard or soft capsule, a liquid, a suspension, an emulsion, a syrup, a powder, a dust, a fine granule, a granule, a pellet, etc., and these formulations may contain, in addition to the active ingredient, a surfactant, a diluent (e.g., lactose, dextrose, sucrose, mannitol, sorbitol, cellulose and glycine) or a lubricant (e.g., silica, talc, stearic acid and a magnesium or calcium salt thereof and polyethylene glycol). The tablet may contain a binder such as magnesium aluminum silicate, starch paste, gelatin, tragacanth, methylcellulose, sodium carboxymethylcellulose and polyvinylpyrrolidine, and may contain, if necessary, a pharmaceutical additive such as a disintegrant, e.g., starch, agar or alginic acid or a sodium salt thereof, an absorbent, a colorant, a flavor, a sweetener, etc. The tablet may be prepared by a common mixing, granulation or coating method.

Formulations for parenteral administration may be, for example, an injection, a medicinal drip, an ointment, a lotion, a gel, a cream, a spray, a suspension, an emulsion, a suppository, a patch, etc., although not being limited thereto.

The pharmaceutical composition according to an exemplary embodiment of the present disclosure may be administered orally or parenterally, e.g., rectally, topically, transdermally, intravenously, intramuscularly, intraperitoneally, subcutaneously, etc. For example, the pharmaceutical composition according to an exemplary embodiment of the present disclosure may be topically administered to the scalp.

A pharmaceutically acceptable dosage, or administration dosage, of the active ingredient will vary depending on the age, sex and body weight of a subject to be treated, a particular disease or pathological condition to be treated, the severity of the disease or pathological condition, administration route and discretion of a diagnoser. Determination of the administration dosage based on these factors is within the level of those skilled in the art. A general administration dosage may be 0.01-1000 mg/kg/day, specifically 1-40 mg/kg/day. However, the scope of the present disclosure is not limited by the administration dosage by any means.

The health food composition according to another exemplary embodiment of the present disclosure may be processed as a fermented milk, a cheese, a yogurt, a juice, a probiotic, a health supplement, etc., and may be used in the form of various other food additives.

The composition may contain other ingredients that provide a synergic effect in addition to the main effect within a range not negatively affecting the main effect. For example, it may further contain additives for improving physical properties, such as a fragrance, a pigment, a disinfectant, an antioxidant, an antiseptic, a humectant, a thickener, a mineral, an emulsifier, a synthetic polymer, etc. In addition, it may further contain adjuvant ingredients such as a water-soluble vitamin, an oil-soluble vitamin, a polypeptide, a polysaccharide, a seaweed extract, etc. These ingredients may be selected by those skilled in the art without difficulty depending on the particular formulation or purpose of use, and the addition amount may be selected within a range not negatively affecting the purpose and effect of the present disclosure.

The composition according to the present disclosure may be prepared into various formulations including a solution, an emulsion, a viscous mixture, a tablet, a powder, etc., and may be administered by various methods, including simple drinking, injection, spraying, squeezing, etc.

In the composition according to an aspect of the present disclosure, the bean may be a germinated and fermented bean which has been germinated and fermented simultaneously or sequentially.

In the composition according to an aspect of the present disclosure, the bean may be one that has been germinated and then fermented.

In the composition according to an aspect of the present disclosure, the germination may be performed by germinating 1-50 vol % of the bean in a reactor containing 20-80 vol % of a medium based on the total volume of the reactor.

In the composition according to an aspect of the present disclosure, the germination may be performed at 20-35° C. under a dark condition for 2-10 days.

In the composition according to an aspect of the present disclosure, the fermentation may be performed by contacting the germinated bean with a microorganism.

In the composition according to an aspect of the present disclosure, the microorganism may be one or more selected from a group consisting of a fungus, yeast and a lactic acid bacterium.

In the composition according to an aspect of the present disclosure, the microorganism may be one or more selected from a group consisting of *Aspergillus niger, Aspergillus sojae, Aspergillus oryzae* and *Bifidobacterium infantis*.

In the composition according to an aspect of the present disclosure, the composition may contain 0.0001-10 wt % of the germinated and fermented bean extract comprising coumestrol based on the total weight of the composition. When the extract is contained in an amount less than 0.0001 wt %, the effect on the climacteric symptom or disease is only slight. And, when it is contained in an amount exceeding 10 wt %, the contents of the other ingredients of the composition are affected. In this regard, the composition may contain 0.001-9.5 wt %, 0.01-9 wt % or 0.1-8.5 wt % of coumestrol based on the total weight of the composition.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

[Example 1] Preparation of Germinated and Fermented Bean Containing Coumestrol and Extract Thereof All the experimental apparatuses were sterilized at 121° C. using a high-pressure sterilizer before inoculation of a microorganism.

Pungsan-namul (sowon-kong, *Glycine max* (L.) Merrill) was used as a bean. The seed of the bean was sterilized by washing twice with sterile water, ethanol and sodium hypochlorite. Then, a medium containing one or more of 1% sucrose, 1% glucose and 1% SRT was prepared with an amount of 20-80 vol % based on the volume of a reactor. For example, when a 10-ton reactor was used, the amount of the medium was 8 tons. The seed of the bean was inoculated with a density of 3-12 vol % based on the volume of the reactor. For example, when a 10-ton reactor was used, the amount of the used seed was 1.2 tons. The seed of the bean was germinated in the reactor containing the medium and the bean seed under a shaded condition of at ° C. while supplying air at a rate of 15000 vvm/m.

On day 2, when the bean began to germinate, 0-1.25 wt % of *Aspergillus oryzae* (Mediogen Co., Ltd., 1×109 CFU/g) based on the total weight of the medium was added to the medium and fermentation was performed until day 8.

Thus obtained germinated and fermented bean was extracted by adding hot water of 80° C. or above and then dried. The resulting germinated and fermented bean extract had a coumestrol concentration of about 0.1%.

[Test Example 1] Improvement of Climacteric Weight Gain by Germinated and Fermented Bean Extract Female hairless mice weighing 26-27 g were used as experimental animals. The experimental animals were bred under a condition of 23±1° C., 40-60% humidity and 12-hour light/dark cycles. Basic feed and drinking water were provided ad libitum. On the previous day before blood taking, drinking water was provided only.

Oophorectomy was conducted aseptically after anesthetizing 15-week-old hairless mice and disinfecting with 70% ethanol. After incising skin tissue about 2-3 cm along the spinal cord below one lateral dorsal part, the muscle and peritoneum at the part where an ovary is located were incised by 1.5 cm to expose the ovary. After removing the ovary, the peritoneum, muscle and skin were sutured using silk suture. The ovary at the opposite side was also removed by the same method. For a control group, a sham operation of incising the muscle and peritoneum but suturing without removal of the ovary was conducted. After the surgical operation, the mice were allowed to recover for a week.

The experimental animals were divided into the control group (sham operation group) and an oophorectomy group. The oophorectomy group was further divided into a germinated and fermented bean extract 500 mg/kg administration group and a coumestrol 0.5 mg/kg administration group, with 10 mice per each group. The administration dosage for the coumestrol administration group was determined such that the amount of coumestrol in the germinated and fermented bean was the same as that of the coumestrol 0.5 mg/kg administration group (content of coumestrol in the germinated and fermented bean extract=0.1%; 500 mg/kg× 0.1%=0.5 mg/kg). For each test group, a feed prepared with the above-described administration dosage was given for 14 weeks to the 16-week-old mice which had passed a week after the oophorectomy until they were 30-week-old.

In general, a climacteric mouse model induced by oophorectomy shows weight gain as compared to a normal group. This phenomenon is also found in women in the climacteric period. It is obvious in the related art that improvement in weight gain in an oophorectomy model can lead to a significant effect in obesity associated with the climacteric period.

Figure 1:
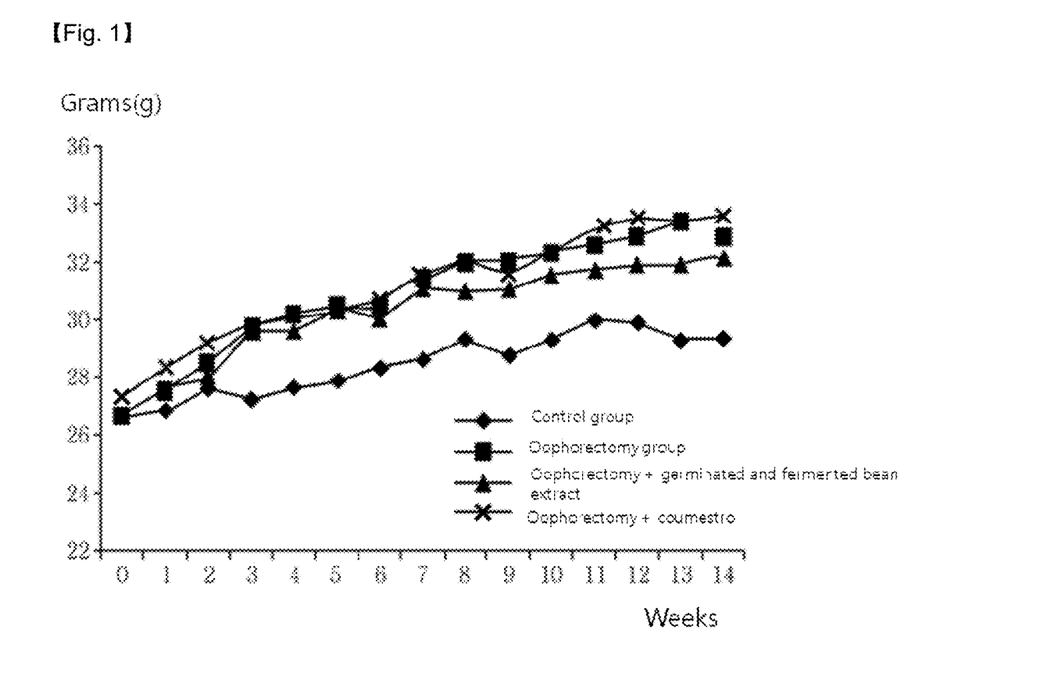
FIG. 1 shows a result of measuring body weight change of climacteric mouse models induced by oophorectomy for 14 weeks (x-axis: weeks, y-axis: grams (g)).

When the body weight of the experimental animals were measured for a total of 14 weeks once a week while giving the above-described feed (FIG. 1), the oophorectomy group showed weight gain by 20% as compared to the normal group. But, the weight gain of the coumestrol administration group was significantly less than that of the oophorectomy group. In addition, as seen from FIG. 1, the germinated and fermented bean extract administration group showed less weight gain than the group to which coumestrol of the same content was administered (that is to say, the germinated and fermented bean extract showed better weight gain improvement effect than coumestrol). This suggests that the germinated and fermented bean extract exhibits a synergic effect provided by a combination of various ingredients in addition to coumestrol.

[Test Example 2] Improvement of Bone Density by Germinated and Fermented Bean Extract In general, bone density decreases in the climacteric period, making the bone break easily even by a slight impact. Therefore, if breaking strength is increased due to increase of the bone density, it can be judged that the climacteric symptom has been improved. A result of measuring the bone density for the same test group (30 weeks old) as that in Test Example 1 by dual-energy X-ray absorptiometry is shown in Table 1.

TABLE 1

| | Bone density (g/cm$^2$) |
|---|---|
| Control group | 0.1975 |
| Oophorectomy group | 0.1821 |
| Oophorectomy + coumestrol administration group | 0.1902 |
| Oophorectomy + germinated and fermented bean extract administration group | 0.1959 |

From Table 1, it can be seen that the bone density of the oophorectomy group, which had decreased by about 8% as compared to the control group, was recovered by the germinated and fermented bean to a level similar to that of the control group. The result for the germinated and fermented bean administration group was superior to that of the group to which coumestrol of the same content was administered, suggesting a synergic effect provided by a combination of various ingredients in the germinated and fermented bean extract.

[Test Example 3] Improvement of Skin Condition Associated with Climacteric Period by Germinated And Fermented Bean Extract

Figure 2:
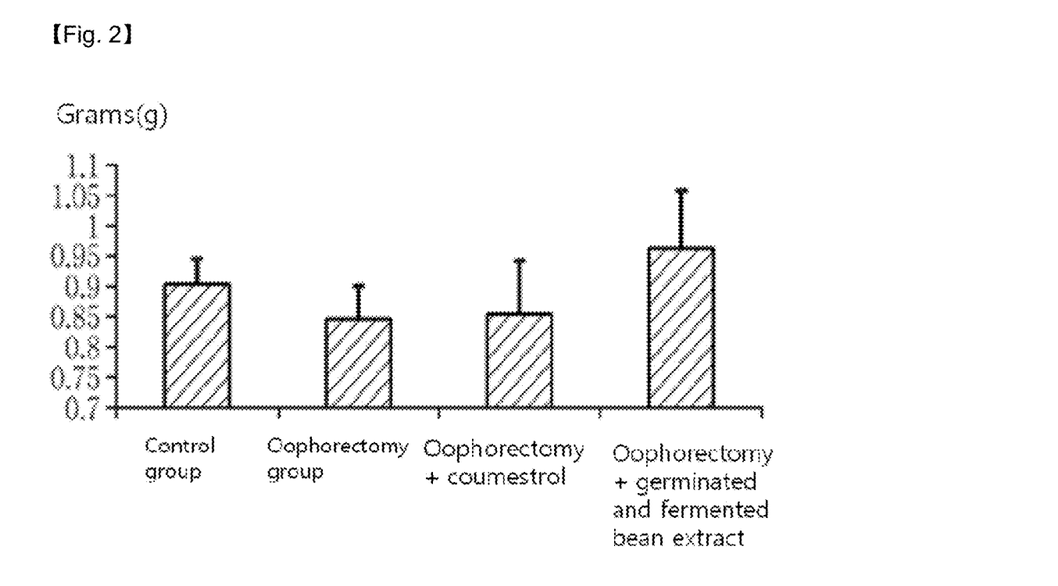
FIG. 2 shows a result of measuring skin thickness of 30-week-old hairless mice a climacteric mouse models induced by oophorectomy (y-axis: grams (g)).

[Test Example 3-1] Improvement in Skin Thickness Decrease Associated with Climacteric Period Skin thickness was measured for the same test group (30 weeks old) as that in Test Example 1 using calipers (HEPT, Cjina). From FIG. 2, it can be seen that the oophorectomy group showed about 10% decreased skin thickness as compared to the control group which had not undergone oophorectomy and that the germinated and fermented bean administration group showed skin thickness nearly similar to that of the control group. The result for the group to which coumestrol of the same content was administered was the same as that of the oophorectomy group. Accordingly, it was confirmed that the intake of the germinated and fermented bean extract provides superior effect of improving skin thickness decrease associated with the climacteric period.

Figure 3:
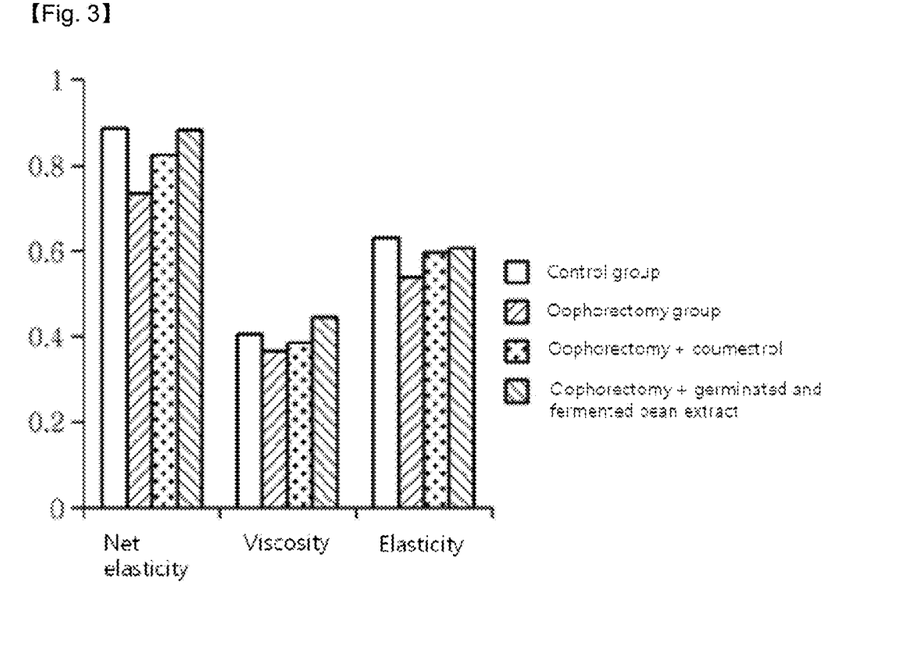
FIG. 3 shows a result of measuring skin elasticity and viscosity of hairless mice in climacteric mouse models induced by oophorectomy (y-axis: unit).

[Test Example 3-2] Improvement in Skin Elasticity Decrease Associated with Climacteric Period Skin elasticity was measured for the same test group (30 weeks old) as that in Test Example 1 using a cutometer (Courage+Khazaka Electronic GmbH, Cologne, Germany). From FIG. 3, it can be seen that the oophorectomy group showed remarkably lower values in all measured items as compared to the control group and that the intake of the germinated and fermented bean extract resulted in recovery to levels very close to that of the control group which had not undergone oophorectomy. In particular, the effect was superior to that of the group to which coumestrol of the same content was administered. Accordingly, it was confirmed that the intake of the germinated and fermented bean extract provides superior effect of improving skin elasticity decrease associated with the climacteric period.

Figure 4:
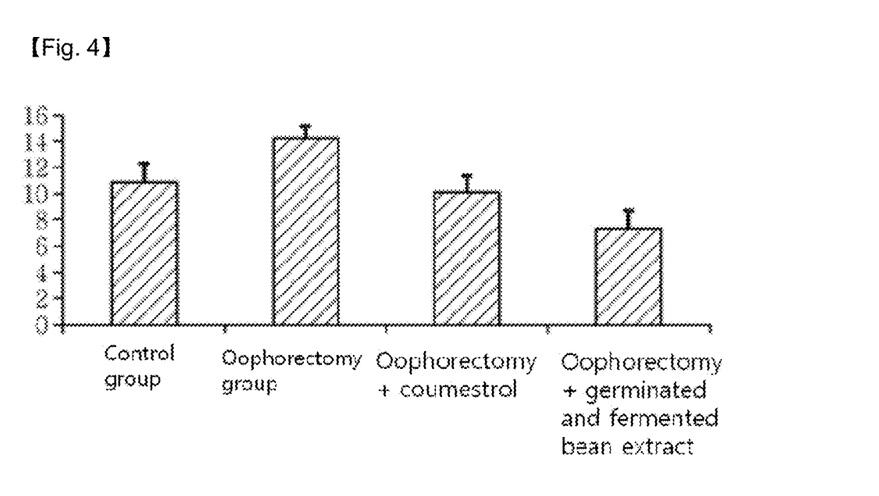
FIG. 4 shows a result of measuring transdermal water loss of hairless mice in climacteric mouse models induced by oophorectomy.

[Test Example 3-3] Improvement in Transepidermal Water Loss Associated with Climacteric Period Transdermal water loss was measured for the same test group (30 weeks old) as that in Test Example 1 using a transdermal water loss meter (Courage+Khazaka Electronic GmbH, Cologne, Germany). From FIG. 4, it can be seen that the oophorectomy group showed about 30% increased transdermal water loss as compared to the control group and that the administration of the germinated and fermented bean extract resulted in significant decrease in transdermal water loss to a level lower than that of the control group which had not undergone oophorectomy. In particular, the effect was superior to that of the group to which coumestrol of the same content was administered. Accordingly, it was confirmed that the intake of the germinated and fermented bean extract provides superior effect of improving transdermal water loss associated with the climacteric period.

[Test Example 4] Activation of Estrogen Receptor by Germinated And Fermented Bean Extract Estrogenic activity of the germinated and fermented bean extract was investigated using the estrogen receptor (reporter assay). A human ER reporter assay kit (Indigo Bioscience) was treated with 100 ppm germinated and fermented bean extract (containing 0.1% coumestrol) or 0.1 ppm coumestrol for 24 hours. A positive control group was treated with 0.1 ppm 17-estradiol. Estradiol acts as a ligand of the estrogen receptor, particularly for ERα (estrogen receptor α) and ERβ (estrogen receptor β). A negative control group ((−) in FIG. 5) was treated with distilled water of the same volume as that of the extract.

Figure 5:
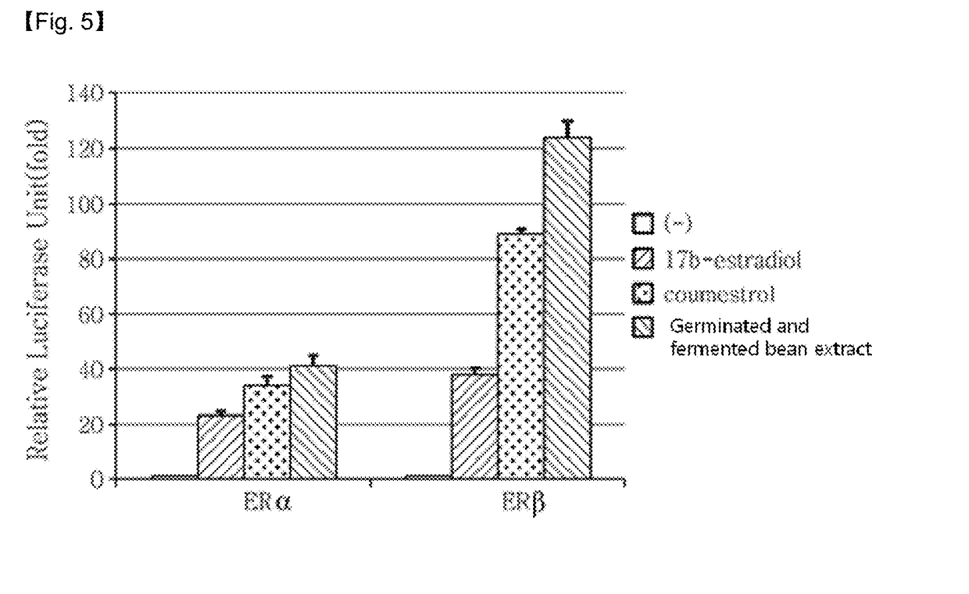
FIG. 5 shows a result of comparing activation of estrogen receptors in test groups.

After the treatment, luciferase activity was measured using the Tecan Infinite M200pro multiplate reader+injector system. The result is shown in FIG. 5.

As a result (FIG. 5), it was confirmed that the group to which the germinated and fermented bean extract was administered showed a binding effect to the estrogen receptor even better than that of estradiol which is the ligand of the estrogen receptor. Accordingly, it is expected that the germinated and fermented bean extract can generate the same signal as estrogen and provide remarkable effect for a climacteric disease or climacteric symptom. The effect of activating the estrogen receptor was superior to the group to which coumestrol of the same content was administered. This is thought to be a synergic effect provided by a combination of various ingredients in the germinated and fermented bean extract.

[Test Example 5] Suppressed Degradation of Collagen by Germinated and Fermented Bean Extract

[Test Example 5-1] Comparison of Expression Levels of IL-6, iNOS and MMP1 Genes

Figure 6:
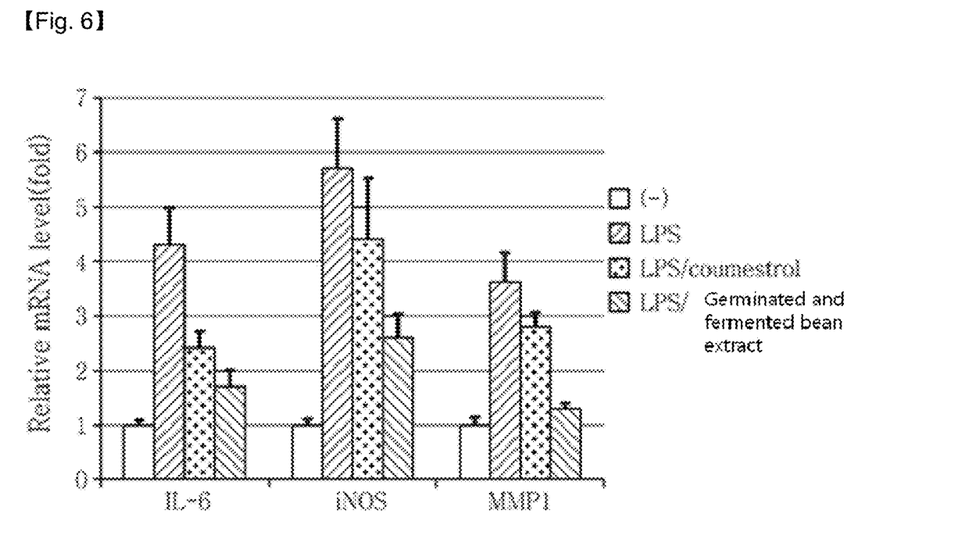
FIG. 6 shows a result of comparing inhibition of MMP1 expression in test groups.

It is known that inflammatory response is increased in the climacteric period in general. Activated inflammatory response leads to increased expression of MMP1 (matrix metalloprotease 1) which degrades collagen, thereby inducing collagen degradation and resulting in decreased skin elasticity. Therefore, by suppressing inflammatory responses, it is possible to maintain skin elasticity by inhibiting collagen degradation. In order to investigate the inflammatory response suppressing effect of coumestrol and a germinated and fermented bean extract containing the same amount of coumestrol, inflammatory response was induced in human dermal fibroblasts by pretreating for 3 hours with 100 ppm germinated and fermented bean extract (containing 0.1% coumestrol) or 0.1 ppm coumestrol and then treating with LPS (lipopolysaccharide; 10 g/mL) for 12 hours. A negative control group ((−) in FIG. 6) was treated with distilled water of the same volume as that of the extract. After extracting RNA using Invitrogen's TRIzol reagent, cDNA was synthesized using Fermentas' reverse transcription kit. Then, the expression of the inflammatory cytokine (IL-6), oxidative stress inducing protein (iNOS) and collagenase (MMP1) genes was quantitated by Q-PCR.

As a result (FIG. 6), it was found out that the levels of the inflammatory cytokine (IL-6) and oxidative stress inducing protein (iNOS) which are associated with inflammatory response and the level of MMP1 which is directly associated with skin elasticity are remarkably reduced by the administration of the germinated and fermented bean extract. The result was even superior to that of the group to which coumestrol of the same content was administered. This confirms a synergic effect provided by a combination of various ingredients in the germinated and fermented bean extract.

[Test Example 5-2] Increase in Procollagen

After recovering cell culture medium from each test group of Test Example 5-1, the amount of procollagen secreted into the medium was measured using Millipore's procollagen ELISA kit.

Figure 7:
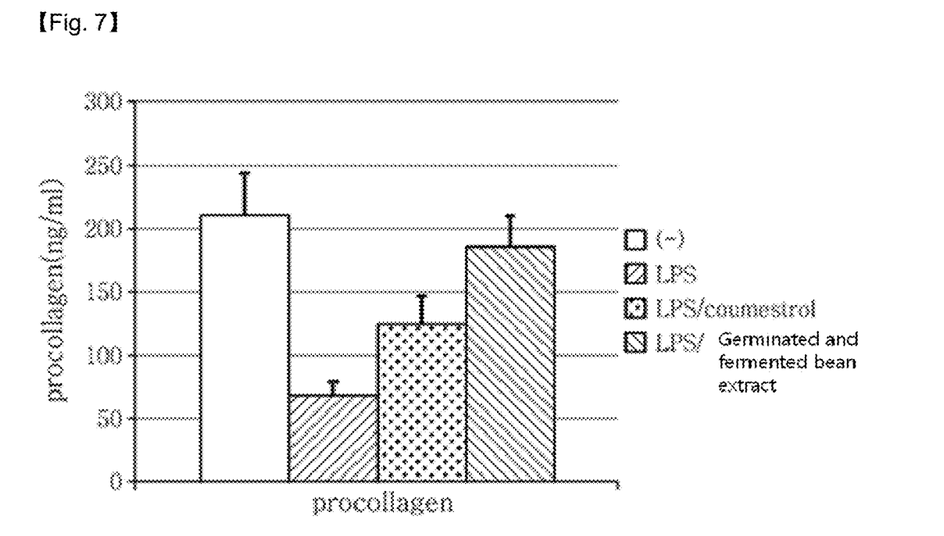
FIG. 7 shows a result of comparing synthesis procollagen in test groups.

As a result (FIG. 7), it was confirmed that the synthesis and secretion of procollagen were significantly increased by the treatment with the germinated and fermented bean extract. The result was even superior to that of the group to which coumestrol of the same content was administered. This confirms a synergic effect provided by a combination of various ingredients in the germinated and fermented bean extract.

[Test Example 6] Improvement of Photoaging by Germinated and Fermented Bean Extract It is known that the skin in the climacteric period is vulnerable to skin irritation such as UV because of decreased skin thickness. 3D artificial skin was prepared and the effect of the germinated and fermented bean extract on the skin was tested after UV irradiation.

A matrix was prepared by mixing $2.64 \times 10^5$ fibroblasts in a collagen solution. After seeding $5 \times 10^6$ keratinocytes thereon, differentiation into artificial skin was induced by treating with 1.2 mM calcium. 2 weeks later, after irradiating 20 mJ UV on the cells and treating with 0.1 ppm coumestrol or 100 ppm germinated and fermented bean extract, the culture medium was recovered and the expression levels of MMP-1 and procollagen were measured in the same manner as in Test Example 5. The result is given in Table 2 relative to the non-UV-irradiated group as 100.

TABLE 2

| | MMP-1 | Procollagen |
|---|---|---|
| Non-UV-irradiated group | 100.0% | 100.0% |
| UV-irradiated group | 142.4% | 68.7% |
| UV irradiation + coumestrol | 122.8% | 82.4% |
| UV irradiation + germinated and fermented bean extract | 108.3% | 95.7% |

From Table 2, it can be seen that the increased MMP-1 expression and decreased procollagen expression induced by the UV irradiation were effectively improved by the treatment with the germinated and fermented bean extract. The group to which coumestrol of the same content was administered showed only slight effect when compared with the germinated and fermented bean administration group. That is to say, the germinated and fermented bean administration group showed a better result than the group to which coumestrol of the same content was administered. This confirms a synergic effect provided by a combination of various ingredients in the germinated and fermented bean extract.

Hereinafter, preparation and formulation examples of the composition according to present disclosure are described. However, the pharmaceutical composition, cosmetic composition or health food composition can be in various forms, and the following examples are non-limiting and for illustrative purposes only.

[Preparation Example 1] Preparation of Soft Capsule

A soft capsule filling solution was prepared by mixing 80 mg of a germinated and fermented bean extract containing coumestrol, 9 mg of vitamin E, 9 mg of vitamin C, 2 mg of palm oil, 8 mg of hydrogenated vegetable oil, 4 mg of yellow beeswax and 9 mg of lecithin according to a commonly employed method. A soft capsule was prepared by filling 400 mg of the solution per capsule. Separately from this, a soft capsule sheet was prepared from 66 parts by weight of gelatin, 24 parts by weight of glycerin and 10 parts by weight of sorbitol solution. Then, the filling solution was filled therein to prepare a soft capsule containing 400 mg of the composition according to the present disclosure.

[Preparation Example 2] Preparation of Tablet 80 mg of a germinated and fermented bean extract containing coumestrol, 9 mg of vitamin E, 9 mg of vitamin C, 200 mg of galactooligosaccharide, 60 mg of lactose and 140 mg of maltose were mixed and granulated using a fluidized-bed drier. After adding 6 mg of sugar ester, 504 mg of the resulting composition was prepared into a tablet according to a commonly employed method.

[Preparation Example 3] Preparation of Drink 80 mg of a germinated and fermented bean extract containing coumestrol, 9 mg of vitamin E, 9 mg of vitamin C, 10 g of glucose, 0.6 g of citric acid and 25 g of oligosaccharide syrup were mixed. After adding 300 mL of purified water, 200 mL of the resulting mixture was filled in a bottle. Then, a drink was prepared by sterilizing at 130° C. for 4-5 seconds.

[Preparation Example 4] Preparation of Granule 80 mg of a germinated and fermented bean extract containing coumestrol, 9 mg of vitamin E, 9 mg of vitamin C, 250 mg of anhydrous crystalline glucose and 550 mg of starch were mixed, granulated using a fluidized-bed drier and filled in a pouch.

[Formulation Example 1] Softening Lotion (Skin Lotion)

TABLE 3

| Ingredients | Contents (wt %) |
|---|---|
| Germinated and fermented bean extract containing coumestrol | 0.0025 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Antiseptic, pigment and fragrance | adequate |
| Purified water | balance |

[Formulation Example 2] Nourishing Lotion (Milk Lotion)

TABLE 4

| Ingredients | Contents (wt %) |
|---|---|
| Germinated and fermented bean extract containing coumestrol | 0.0025 |

TABLE 4-continued

| Ingredients | Contents (wt %) |
| --- | --- |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Antiseptic, pigment and fragrance | adequate |
| Purified water | balance |

[Formulation Example 3] Nourishing Cream

TABLE 5

| Ingredients | Contents (wt %) |
| --- | --- |
| Germinated and fermented bean extract containing coumestrol | 0.0025 |
| Glycerin | 3.0 |
| Butylene glycol | 3.0 |
| Liquid paraffin | 7.0 |
| Beta-glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Antiseptic, pigment and fragrance | adequate |
| Purified water | balance |

[Formulation Example 4] Massage Cream

TABLE 6

| Ingredients | Contents (wt %) |
| --- | --- |
| Germinated and fermented bean extract containing coumestrol | 0.0025 |
| Glycerin | 8.0 |
| Butylene glycol | 4.0 |
| Liquid paraffin | 45.0 |
| Beta-glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |
| Antiseptic, pigment and fragrance | adequate |
| Purified water | balance |

[Formulation Example 5] Pack

TABLE 7

| Ingredients | Contents (wt %) |
| --- | --- |
| Germinated and fermented bean extract containing coumestrol | 0.0025 |
| Glycerin | 4.0 |
| Polyvinyl alcohol | 15.0 |
| Hyaluronic acid extract | 5.0 |
| Beta-glucan | 7.0 |
| Allantoin | 0.1 |
| Nonyl phenyl ether | 0.4 |
| Polysorbate 60 | 1.2 |
| ethanol antiseptic | 6.0 adequate |
| Antiseptic, pigment and fragrance | adequate |
| Purified water | balance |

[Formulation Example 6] Ointment

TABLE 8

| Ingredients | Contents (wt %) |
| --- | --- |
| Germinated and fermented bean extract containing coumestrol | 0.0025 |
| Glycerin | 8.0 |
| Butylene glycol | 4.0 |
| Liquid paraffin | 15.0 |
| Beta-glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Antiseptic, pigment and fragrance | adequate |
| Purified water | balance |

While the exemplary embodiments have been shown and described, it will be understood by those skilled in the art that various changes in form and details may be made thereto without departing from the spirit and scope of this disclosure as defined by the appended claims.

INDUSTRIAL APPLICABILITY

The present disclosure relates to a composition for preventing a climacteric disease, which contains a bean extract containing coumestrol as an active ingredient. More particularly, it relates to a composition for preventing a climacteric disease, which contains a germinated and fermented bean extract containing coumestrol as an active ingredient. The composition of the present disclosure, which contains a germinated and fermented bean extract containing coumestrol as an active ingredient, can be usefully used to prevent, treat and improve a climacteric disease or a climacteric symptom. Specifically, the composition of the present disclosure can relieve weight gain during the climacteric period, can recover bone density to a level similar to that before the climacteric period and can relieve decrease in skin thickness and skin elasticity during the climacteric period. In addition, since the composition of the present disclosure can also relieve transepidermal water loss during the climacteric period, can activate estrogen and can decrease the amount of MMP1 which degrades collagen and increase the amount of procollagen at the same time, it can be usefully used for a climacteric disease or a climacteric symptom. Also, the composition of the present disclosure, which contains a natural product as an active ingredient, lacks tolerance even when used for a long time and has few side effects.

The invention claimed is:

1. A method for preventing or improving a climacteric skin symptom, wherein the method comprises administering an effective amount of a germinated and fermented bean extract comprising coumestrol to a subject in need thereof, wherein the method is for preventing or improving a climacteric skin symptom, which is UV-induced skin irritation, and
wherein the fermentation is performed by contacting the germinated bean with *Aspergillus oryzae*.

2. The method according to claim 1, wherein the germinated and fermented bean is a bean which has been germinated and fermented simultaneously or sequentially.

3. The method according to claim 1, wherein the bean has been germinated and then fermented.

4. The method according to claim 1, wherein the germination is performed by germinating 1-50 vol % of the bean in a reactor comprising 20-80 vol % of a medium based on the total volume of the reactor.

5. The method according to claim 1, wherein the germination is performed at 20-35° C. under a dark condition for 2-10 days.

6. The method according to claim 1, wherein the germinated and fermented bean extract comprising coumestrol is administered in form of a composition comprising 0.0001-10 wt % of the germinated and fermented bean extract comprising coumestrol based on the total weight of the composition.

7. The method according to claim 1, wherein the germinated and fermented bean extract comprising coumestrol is administered in form of a pharmaceutical composition.

8. The method according to claim 1, wherein the germinated and fermented bean extract comprising coumestrol is administered in form of a health food composition.

9. The method according to claim 1, wherein the germinated and fermented bean extract comprising coumestrol is administered in form of a cosmetic composition.

* * * * *

UNITED STATES PATENT AND TRADEMARK OFFICE
CERTIFICATE OF CORRECTION

PATENT NO. : 10,959,981 B2  
APPLICATION NO. : 15/989544  
DATED : March 30, 2021  
INVENTOR(S) : Hyun Jung Shin et al.

Page 1 of 1

It is certified that error appears in the above-identified patent and that said Letters Patent is hereby corrected as shown below:

On the Title Page

Column 1, (30) Foreign Application Priority Data:  
"May 2, 2014 (KR) .................. 10-2014-0053471"  
Should read:  
-- May 6, 2013 (KR) ................. 10-2014-0050771  
May 2, 2014 (KR) .................. 10-2014-0053471 --

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*